US008609904B2

(12) United States Patent
Devaux et al.

(10) Patent No.: US 8,609,904 B2
(45) Date of Patent: Dec. 17, 2013

(54) PROCESS FOR MANUFACTURING ACROLEIN AND/OR ACRYLIC ACID FROM GLYCEROL

(75) Inventors: Jean-Francois Devaux, Soucieu en Jarrest (FR); Michel Fauconet, Valmont (FR); Nabil Tlili, Mulhouse (FR); Philippe Haller, Saint-Avold (FR); Jean-Paul Combet, Villefranche sur Saone (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 13/515,047

(22) PCT Filed: Dec. 13, 2010

(86) PCT No.: PCT/FR2010/052692
§ 371 (c)(1),
(2), (4) Date: Aug. 13, 2012

(87) PCT Pub. No.: WO2011/080447
PCT Pub. Date: Jul. 7, 2011

(65) Prior Publication Data
US 2012/0302797 A1 Nov. 29, 2012

Related U.S. Application Data

(60) Provisional application No. 61/314,234, filed on Mar. 16, 2010.

(30) Foreign Application Priority Data

Dec. 14, 2009 (FR) ...................................... 09 58937

(51) Int. Cl.
C07C 45/78 (2006.01)
C07C 45/82 (2006.01)
C07C 51/16 (2006.01)

(52) U.S. Cl.
USPC ........................................... 568/486; 562/432

(58) Field of Classification Search
USPC ........................................... 568/486; 562/532
See application file for complete search history.

(56) References Cited

U.S. PATENT DOCUMENTS

| 6,348,638 | B1 | 2/2002 | Schliephake et al. |
| 2009/0134357 | A1 | 5/2009 | Bub et al. |
| 2010/0168471 | A1 | 7/2010 | Dubois |

OTHER PUBLICATIONS

Studies in Surface Science and Catalysis vol. 51—New Solid Acids and Bases; Their Catalytic Properties—Kozo Tanabe, Makoto Misono, Yoshio Ono, Hideshi Hattori—pp. 1-24, (1989).
Daniel Ballerini et Gerard Hillion—Pactualite Chimique Nov./Dec. 2002 "Methanolysis of Vegetable Oils" (6 Pages).

*Primary Examiner* — Sikarl Witherspoon
(74) *Attorney, Agent, or Firm* — Lynn B. Morreale

(57) ABSTRACT

The present invention relates to the manufacture of bioresourced acrolein and bioresourced acrylic acid from glycerol as starting material and more particularly comes within the scope of a process for the manufacture of acrolein and acrylic acid according to which the reaction for the dehydration of glycerol to give acrolein is carried out and a stage of oxidizing a water-rich phase separated from the reaction mixture coming from this dehydration reaction is carried out, before it is recycled to the glycerol dehydration stage. This oxidation treatment prevents organic impurities from accumulating during the process, while minimizing the consumption of water and the discharge of polluted aqueous streams.

14 Claims, 4 Drawing Sheets

PROCESS FOR MANUFACTURING ACROLEIN AND/OR ACRYLIC ACID FROM GLYCEROL

FIELD OF THE INVENTION

Figure 1:
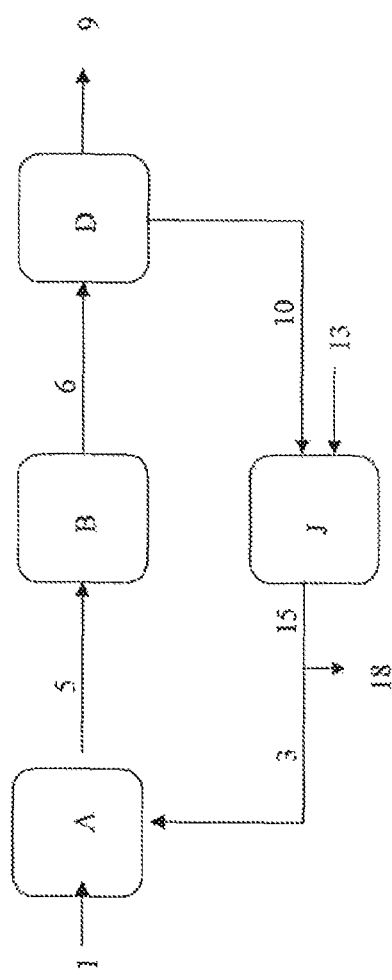

The present invention relates to the manufacture of bioresourced acrolein and bioresourced acrylic acid from glycerol as starting material and more particularly comes within the scope of a process for the manufacture of acrolein and acrylic acid according to which the reaction for the dehydration of glycerol to give acrolein is carried out and a stage of oxidizing a water-rich phase separated from the reaction mixture coming from this dehydration reaction is carried out, before it is recycled to the glycerol dehydration stage. This oxidation treatment prevents organic impurities from accumulating during the process, while minimizing the consumption of water and the discharge of polluted aqueous streams.

PRIOR ART

The process for the synthesis of acrylic acid most widely employed industrially uses a catalytic reaction of propylene using an oxygen-containing mixture. This reaction is generally carried out in a vapour phase and most often in two stages: the first stage carries out the substantially quantitative oxidation of the propylene to give an acrolein-rich mixture in which acrylic acid is a minor component and then the second stage carries out the selective oxidation of the acrolein to give acrylic acid. The reaction conditions of these two stages, carried out in two reactors in series or in the two reaction regions of a single reactor, are different and require catalysts suited to each of the reactions.

For some years, manufacturers have been carrying out research and development studies on processes for the synthesis of acrolein and acrylic acid using bioresourced starting materials. These studies arise from the concern to avoid the use in the future of fossil starting materials, such as propylene, the petroleum origin of which is contributing to global warming due to the greenhouse effect. Furthermore, its cost can only increase in the future with the decline in global oil reserves.

Mention may be made, among these alternative processes starting from non-fossil starting materials, of the processes using, as starting material, 3-hydroxypropionic acid obtained by fermentation of glucose or molasses from biomass.

Mention may also be made of the processes starting from glycerol (also known as glycerin) resulting from the methanolysis of vegetable oils at the same time as the methyl esters, which are themselves employed in particular as fuels in gas oil and domestic heating oil. This glycerol is a natural product which enjoys a "green" aura, it is available in large amounts and it can be stored and transported without difficulty. The methanolysis of vegetable oils or animal fats can be carried out according to various well known processes, in particular by using homogeneous catalysis, such as sodium hydroxide or sodium methoxide in solution in methanol, or by using heterogeneous catalysis. Reference may be made on this subject to the paper by D. Ballerini et al. in l'Actualité Chimique of November-December 2002.

The processes using 3-hydroxypropionic acid as starting material have a major disadvantage from an economic viewpoint. They involve a fermentation reaction which is necessarily carried out under highly dilute conditions in water. In order to obtain acrylic acid, a very large amount of water has to be removed by distillation, at the price of a very high energy cost. Furthermore, the energy expended to separate the water, which energy is produced from fossil material, will be highly damaging to the initial advantage of producing acrylic acid from this bioresourced starting material. Mention may be made, in this field, of Application WO 2006/092271, which describes a process for the production of polymers from acrylic acid prepared by the enzymatic route, in particular from carbohydrate.

Glycerol is recognized today as suitable starting material for envisaging the industrial manufacture of bioresourced acrolein and bioresourced acrylic acid.

The reaction involved in order to obtain acrolein from glycerol is:

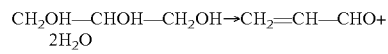
$CH_2OH-CHOH-CH_2OH \rightarrow CH_2=CH-CHO + 2H_2O$

This stage is followed by an oxidation of the acrolein in order to obtain the acrylic acid.

Various processes for the synthesis of acrolein from glycerol are described in the literature. Mention may be made of the documents FR 695 931, U.S. Pat. No. 2,558,520, WO 99/05085, U.S. Pat. No. 5,387,720, WO 06/087083, WO 06/087084 and WO 09/044,081.

In Patent Application EP 1 710 227, the reaction product resulting from the reaction for the dehydration of glycerol in the gas phase is subjected to a subsequent stage of oxidation in the gas phase in order to obtain acrylic acid. The process is carried out in two reactors in series, each comprising a catalyst suited to the reaction being carried out. It is recommended to add oxygen to the gas mixture feeding the second reactor, in order to improve the oxidation reaction and to obtain the acrylic acid with a high yield. This two-stage process is carried out with pure glycerol or with aqueous solutions comprising more than 50% by weight of glycerol. It is advisable to use a concentrated glycerol solution in order to limit the energy cost related to the evaporation of the aqueous solution and the cost related to the treatment of the wastewater. However, if the concentration of glycerol is too high, there is a risk that more side reactions will take place, resulting in numerous by-products, such as the formation of glycerol ethers or reactions between the acrolein produced or the acrylic acid produced and the glycerol. These heavy by-products have a tendency to remain on the dehydration catalyst and they result in coking of the catalyst and in its very rapid deactivation.

Application WO 06/136336 describes a process for the synthesis of acrolein and acrylic acid in which the dehydration reaction is followed by a stage of separation into an acrolein-enriched phase and an acrolein-depleted phase, the latter phase, which is rich in water, being returned upstream of the dehydration reactor in order to dilute the glycerol and to obtain an aqueous phase comprising less than 10% of glycerol.

In this Application WO 06/136336, which relates essentially to a liquid-phase dehydration process, the acrolein-depleted and water-rich phase also comprises heavier compounds formed during the dehydration reaction which have a tendency to form, in the reaction stage, heavy compounds which foul the catalyst and bring about its deactivation.

International Application WO 2006/092272 describes a process for the preparation of acrylic acid from glycerol comprising either a stage of dehydration of the glycerol in the liquid phase or a stage of dehydration in the gas phase. The reaction mixture comprising the acrolein obtained from the reaction for the dehydration of the glycerol is brought into contact with water in a quench unit before being sent to the oxidation reactor. In the presence of a large stream of water, there is a risk that the oxidation catalyst of acrolein will rapidly lose its effectiveness and its mechanical strength, making it difficult to maintain such a process. According to FIG. 5 of this document, the reaction mixture resulting from the liquid-phase dehydration is subjected to a distillation which separates, on the one hand, the light products with a boiling point lower than that of the acrolein and, on the other hand, a fraction comprising the heavy products with a boiling point greater than that of the acrolein, this second fraction, which is rich in water, being returned to the reaction stage after having removed the impurities in a separator equipped with a membrane. The principle of such recycling can nevertheless result in the accumulation of some impurities in the water loop thus generated, due to the lack of selectivity of the membrane or to the fouling thereof.

Application WO 08/087,315 describes a process for the preparation of acrylic acid from glycerol in two stages, in which use is made of an intermediate stage consisting in condensing, at least in part, the water and the heavy by-products present in the stream resulting from the first dehydration stage, before sending the stream to the oxidation reactor. This process makes it possible to use dilute aqueous glycerol solutions, producing a beneficial effect on the dehydration reaction, while limiting possible damage to the catalyst for the oxidation of acrolein in the presence of an excessively large amount of water. The aqueous stream thus generated by the condensation stage is sent, in all or part, either to a rectification column, in order to recover the light products possibly present, or to a port for the treatment of wastewater exhibiting, however, the disadvantage of expensive treatments before discharge into the natural environment of large amounts of aqueous effluents. Alternatively, this stream can be sent to a thermal oxidizer where it is incinerated. The use of the gaseous vents from the thermal oxidation is not described. In another situation, a portion of this aqueous stream may be recycled directly in order to dilute the glycerol to the desired concentration, in which case impurities may accumulate in the water loop thus formed and the risk may exist of coking of the dehydration catalyst.

Document U.S. Pat. No. 6,348,638 discloses a thermal oxidation carried out on a gas stream containing by-products of lower boiling point than that of acrylic acid, including acrolein, formed during the preparation of acrylic acid from propylene. This phase does not contain a substantial proportion of water and heavy by-products having a boiling point above that of acrolein, such as those arising from the dehydration of glycerol. Moreover, the above document does not describe the reinjection (or reutilization) in the process of the gaseous vents from the thermal oxidation. Energy recovery is envisaged via the use of several heat exchangers between the gaseous vents on the one hand and the streams in the process on the other. The use of several heat exchangers makes the process expensive.

The present invention proposes to overcome the disadvantages exhibited by the abovementioned processes for the manufacture of acrylic acid in order to significantly improve the process for the manufacture of acrylic acid, comprising a first stage of dehydration of glycerol to give acrolein, followed by a stage of oxidation of the acrolein to give acrylic acid, with regard to the following points:

reduction in the consumption of water, while ensuring optimization of the reaction for the dehydration of glycerol in the presence of water;

limitation of polluted aqueous discharges;

reduction in the energy consumption and in the size of the installations;

limitation of the losses of product while ensuring efficient recovery of the reaction products;

increase in the cycle period of the dehydration and oxidation catalysts.

For this purpose, it is proposed to separate the aqueous stream coming from the glycerol dehydration reaction into an acrolein-rich phase and an aqueous phase depleted in acrolein and rich in water and heavy by-products and to send the said aqueous phase to an oxidizer before being at least partly recycled to the dehydration stage, thus making it possible to limit the consumption of water and the accumulation of heavy organic impurities on the dehydration catalyst, but also to recover the heat generated by the oxidation of the organic impurities contained in the aqueous phase.

SUMMARY OF THE INVENTION

One subject therefore of the present invention is a process for the manufacture of acrolein from glycerol comprising at least the following stages:

a) glycerol is subjected to a dehydration reaction in order to obtain an aqueous stream comprising acrolein;

b) the stream resulting from stage a) is separated into an acrolein-rich phase and an acrolein-depleted aqueous phase; and c) all or part of the acrolein-depleted aqueous phase is recycled to stage a), characterized in that an oxidation stage is carried out, in the presence of oxygen, an oxygen-containing gas, hydrogen peroxide or ozone, on the said acrolein-depleted aqueous phase before being recycled to stage a).

Another subject of the invention is a process for the manufacture of acrylic acid from glycerol comprising at least the following stages:

a) glycerol is subjected to a dehydration reaction in order to obtain an aqueous stream comprising acrolein;

b) the stream resulting from stage a) is separated into an acrolein-rich phase and an acrolein-depleted aqueous phase;

c) all or part of the acrolein-depleted aqueous phase is recycled to stage a);

d) the acrolein-rich phase is subjected to a catalytic oxidation reaction in order to obtain a stream comprising acrylic acid;

e) the stream resulting from stage d) is subjected to one or more purification treatments and purified acrylic acid is recovered, characterized in that an oxidation stage is carried out, in the presence of oxygen, an oxygen-containing gas, hydrogen peroxide or ozone, on said acrolein-depleted aqueous phase before being recycled to stage a).

Figure 2:
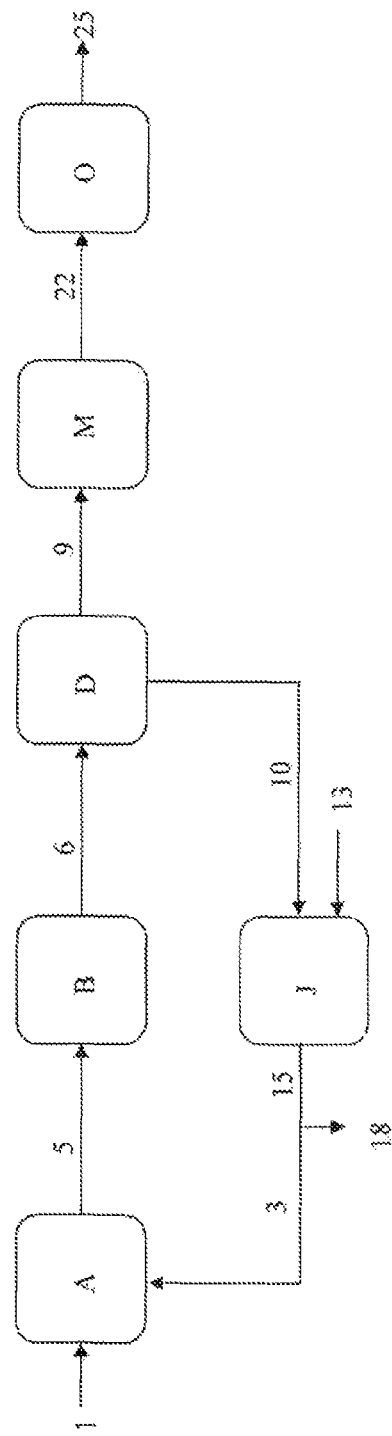
Figure 3:
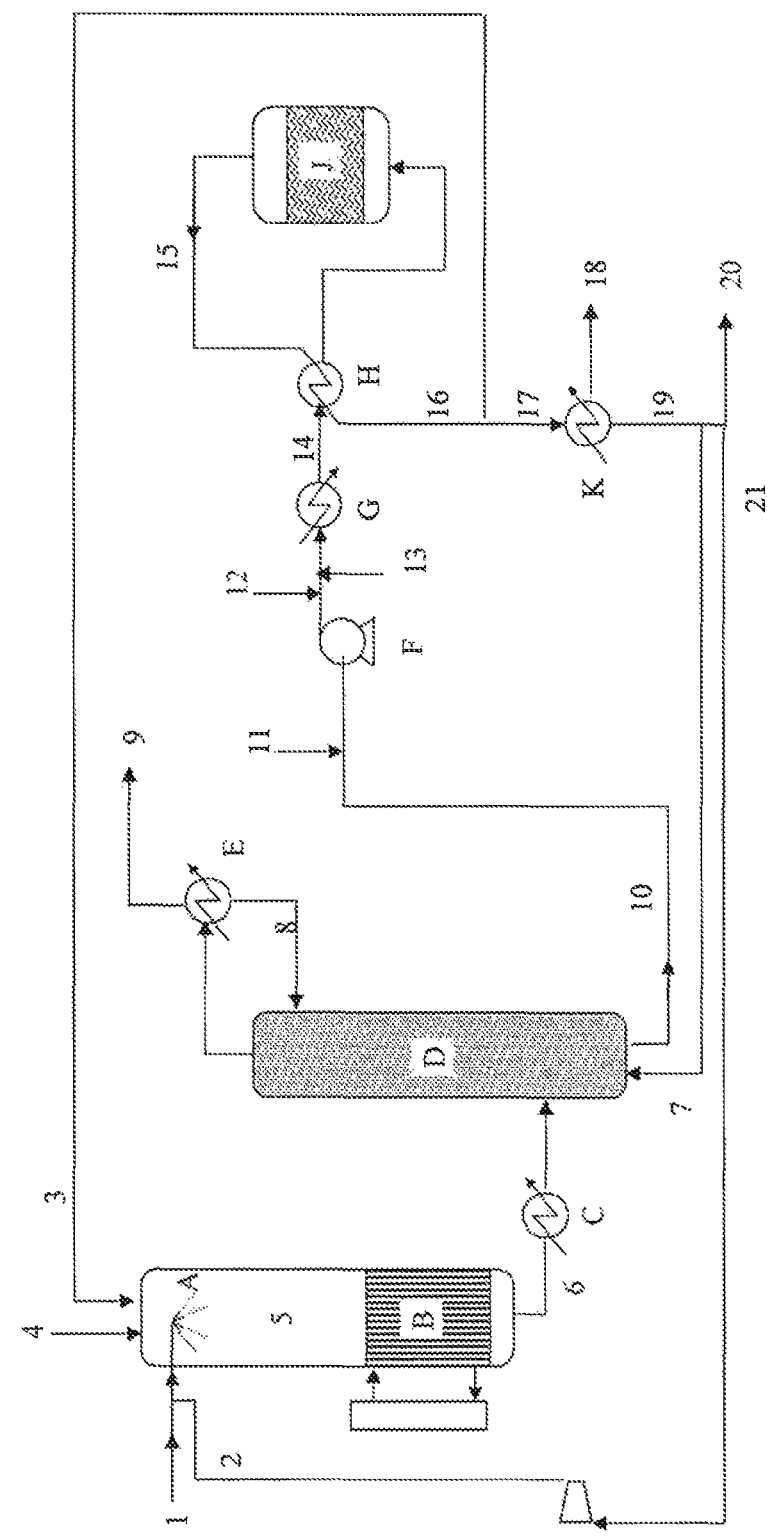
Figure 4:
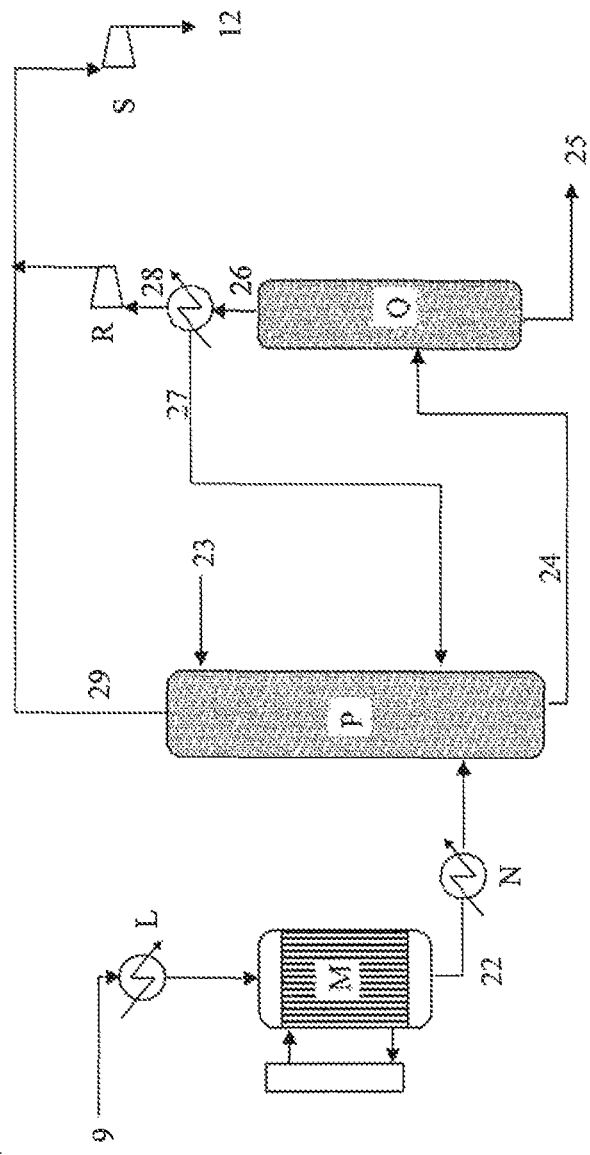
Figure 5:
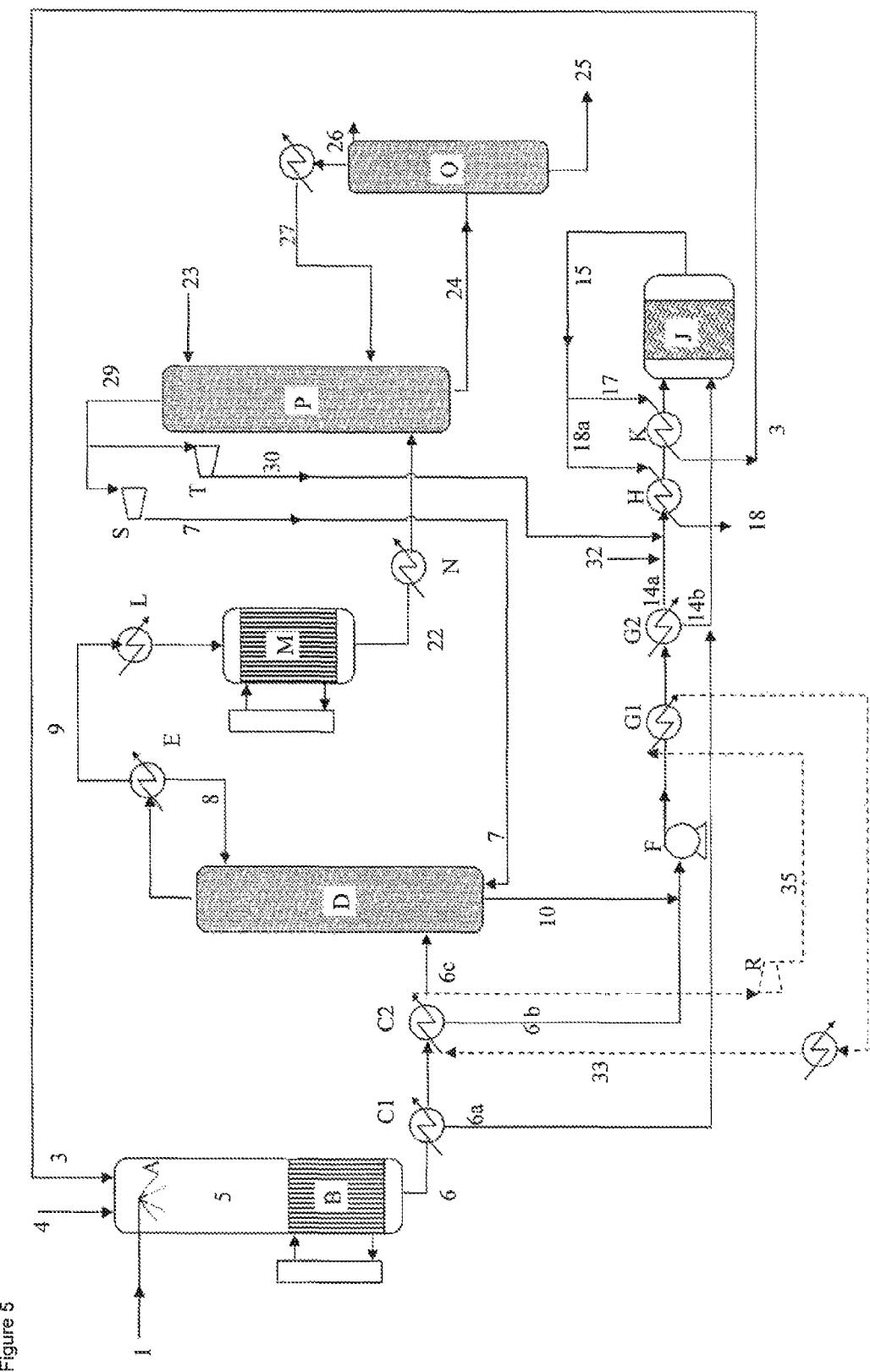

Other features and advantages of the invention will more clearly emerge on reading the detailed description which follows and the nonlimiting implementational examples of the invention, with reference to the appended figures, which represent:

FIG. 1: a block diagram of the process for the manufacture of acrolein according to the invention;

FIG. 2: a block diagram of the process for the manufacture of acrylic acid according to the invention;

FIG. 3: a detailed diagram of a preferred embodiment of the process for the manufacture of acrolein according to the invention;

FIG. 4: a detailed diagram of stages d) and e) of the process for the manufacture of acrylic acid according to the invention and FIG. 5: a detailed diagram of a preferred embodiment of the process for the manufacture of acrylic acid according to the invention.

DETAILED DESCRIPTION OF THE INVENTION

Manufacture of Acrolein

With reference to FIG. 1, for implementing the process according to the invention use is generally made, for feeding the reactor (B) of stage a) for dehydration of glycerol, of a stream (5) comprising the glycerol and water, with a water/glycerol ratio by weight which can vary with wide limits, for example between 0.04/1 and 9/1 and preferably between 0.7/1 and 5/1. The stream (5) can also comprise oxygen, nitrogen and $CO_2$. This stream (5) is advantageously obtained during a stage of mixing (A) a stream (1) rich in glycerol and a phase (3) rich in recycled water which can comprise nitrogen, oxygen, argon and $CO_2$. The stream (1) can, for example, be crude commercial glycerol (glycerin), that is to say typically comprising 80-90% of glycerol, 1 to 10% of salts, 1 to 4% of non-glycerin organic matter, including methanol, and 3 to 15% of water. Use is advantageously made of desalted glycerol, which can be obtained from crude glycerol by any means known to a person skilled in the art, such as distillation under reduced pressure or flash distillation under reduced pressure or separation using ion-exchange resins, such as described, for example, in Application EP 1 978 009. It is also possible to start from salt-free glycerin obtained by processes for the transesterification of oils catalysed by heterogeneous catalysts. It is also possible to use refined glycerin with a purity of greater than 98%, 99% or 99.5%. It is also possible to use an aqueous solution comprising from 20 to 99% by weight, preferably from 30 to 80% by weight, of glycerol.

The dehydration reaction, stage a), which is favoured by a high temperature level, is generally carried out in the gas phase in the reactor (B) in the presence of a catalyst at a temperature ranging from 150° C. to 500° C., preferably between 250° C. and 350° C., and at a pressure of between $10^5$ and $5\times10^5$ Pa (1 and 5 bar). It can also be carried out in the liquid phase; in this case, the temperature is between 150° C. and 350° C. under a pressure ranging from $5\times10^5$ to $100\times10^5$ Pa. Preferably, this first stage is carried out in the gas phase.

It is also possible to carry it out in the presence of oxygen or of a gas comprising oxygen, as described in applications WO 06/087083 and WO 06/114506. In this case, the amount of oxygen is chosen so as to be outside the flammability range at any point of the plant. The molar ratio of molecular oxygen to glycerol is generally of the order of 0.1 to 1.5, preferably from 0.3 to 1.0. The oxygen or the oxygen-containing gas may be partly or completely supplied by the stream (3).

The dehydration reaction can also be carried out in a reaction medium comprising a gas phase comprising from 1 to 3000 ppm of a compound which is an acid within the meaning of the Pearson classification chosen, for example, from $SO_3$, $SO_2$ or $NO_2$, the dehydration reaction being carried out either in the gas phase or in the liquid phase.

The reaction for the dehydration of glycerol is generally carried out over solid acid catalysts. The catalysts which are suitable are homogeneous or multiphase substances which are insoluble in the reaction medium and which have a Hammett acidity, denoted $H_0$, of less than +2. As indicated in U.S. Pat. No. 5,387,720, which refers to the paper by K. Tanabe et al. in "Studies in Surface Science and Catalysis", Vol. 51, 1989, chap. 1 and 2, the Hammett acidity is determined by amine titration using indicators or by adsorption of a base in the gas phase.

These catalysts can be chosen from natural or synthetic siliceous substances or acidic zeolites; inorganic supports, such as oxides, covered with mono-, di-, tri- or polyacidic inorganic acids; oxides or mixed oxides or heteropolyacids or heteropolyacid salts.

These catalysts can in particular be composed of a heteropolyacid salt in which the protons of said heteropolyacid are exchanged with at least one cation chosen from elements belonging to Groups I to XVI of the Periodic Table of the Elements, these heteropolyacid salts comprising at least one element chosen from the group consisting of W, Mo and V.

Mention may particularly be made, among mixed oxides, of those based on iron and on phosphorus and of those based on caesium, phosphorus and tungsten.

The catalysts are chosen in particular from zeolites, Nafion® composites (based on sulphonic acid of fluoropolymers), chlorinated aluminas, phosphotungstic and/or silicotungstic acids and acid salts, and various solids of the type comprising metal oxides, such as tantalum oxide $Ta_2O_5$, niobium oxide $Nb_2O_5$, alumina $Al_2O_3$, titanium oxide $TiO_2$, zirconia $ZrO_2$, tin oxide $SnO_2$, silica $SiO_2$ or silicoaluminate $SiO_2/Al_2O_3$, impregnated with acid functional groups, such as borate $BO_3$, sulphate $SO_4$, tungstate $WO_3$, phosphate $PO_4$, silicate $SiO_2$ or molybdate $MoO_3$ functional groups, or a mixture of these compounds.

The preceding catalysts can additionally comprise a promoter, such as Au, Ag, Cu, Pt, Rh, Pd, Ru, Sm, Ce, Yt, Sc, La, Zn, Mg, Fe, Co, Ni or montmorillonite.

The preferred catalysts are phosphated zirconias, tungstated zirconias, silica zirconias, titanium or tin oxides impregnated with tungstate or phosphotungstate or silicotungstate, phosphated aluminas or silicas, heteropolyacids or heteropolyacid salts, iron phosphates and iron phosphates comprising a promoter.

It is also possible to carry out the reaction for the dehydration of glycerol in the presence of an amount of hydrogen ranging from 0.1 to 10% by volume with respect to the reaction mixture and, in this case, in the presence of a catalyst chosen from those described in application US 2008/018319.

The reactor (B) used can operate as a fixed bed, as a moving bed, as a fluidized bed or as a circulating fluidized bed or in a configuration as modules (sheets or pans). The contact time, expressed in seconds, is the ratio between the volume of the catalyst bed and the volume of the gaseous reactants conveyed per second. The average temperature and pressure conditions existing in a bed can vary according to the nature of the catalyst, the nature of the catalytic bed and the size of the catalyst. In general, the contact time is from 0.1 to 20 seconds and preferably from 0.3 to 15 seconds.

On completion of stage a), an aqueous stream (6), which can be liquid or gaseous and which comprises the desired acrolein, water, unreacted glycerol and by-products, such as hydroxypropanone, propanaldehyde, acetaldehyde, formaldehyde, acrylic acid, propionic acid, acetic acid, formic acid, acetone, phenol, addition products of acrolein with glycerol, polycondensation products of glycerol or cyclic glycerol ethers, and also light compounds, such as nitrogen, oxygen, carbon monoxide, carbon dioxide and argon, is obtained. Some of these products are heavy compounds and others are condensable light compounds. Others are light compounds which cannot be condensed under the temperature and pressure conditions normally employed.

The stream (6) has a high water content due to the composition of the stream (5) entering the reactor (glycerol charge) and to the reaction itself (dehydration). Stage b) in the process according to the invention consists in separating this stream (6) into a phase (9) enriched in acrolein and a phase (10) rich in water and depleted in acrolein. This stage b), such as the partial condensation of the water described, for example, in Patent Application WO 08/087,315 on behalf of the Applicant Company or such as the separation described in Application WO 2006/136336, has the aim of removing most of the water present and the heavy by-products before sending the stream comprising the acrolein to a purification stage, in a process for the manufacture of acrolein, or to the stage for the oxidation of acrolein to give acrylic acid, in a two-stage process for the manufacture of acrylic acid from glycerol. This partial separation of the water thus makes it possible to avoid damage to the catalyst of the 2nd stage for the oxidation of acrolein to give acrylic acid and to avoid, during the subsequent stages, the removal of large amounts of water, which could well be expensive and result in losses of acrylic acid. In addition, it makes it possible to remove a portion of the "heavy" impurities formed during the dehydration of the glycerol.

This stage b) is carried out on a separating unit (D). In the case where stage a) was carried out in the gas phase, the separating unit (D) is a condensation plant which can comprise an absorption column coupled or not coupled to an evaporator, a heat exchanger, a condenser, a dephlegmator, and any item of equipment well known to a person skilled in the art which makes it possible to carry out a partial condensation of an aqueous stream. It is carried out under conditions such that from 20 to 95%, preferably from 40 to 90%, of the water present in the stream (6) is removed in the liquid stream (10). The gas stream (9) generally comprises more than 80% and preferably more than 90% of the acrolein initially present in the stream (6). This result is obtained by lowering the temperature to a temperature of 60 to 120° C.

In the case where stage a) was carried out in the liquid phase under pressure, stage b) can be carried out by a reduction in pressure to a pressure of 1 to 4 bar, optionally coupled to a heat exchanger and a gas-liquid separation plant which can be a flash drum, a distillation column or any other device known to a person skilled in the art. A liquid stream (10) is recovered which comprises from 20 to 95%, preferably from 40 to 90%, of the water present in the stream (6) and a gas stream (9) which comprises more than 80% and preferably more than 90% of the acrolein initially present in the stream (6).

The condensed phase (10) thus generated generally comprises from 90 to 99% of water, the remainder representing acrolein and impurities, such as acrylic acid, glycerol, acetic acid, hydroxypropanone, propionic acid and other heavy organic compounds.

One of the objects of the process of the invention is to obtain a water-rich and acrolein-depleted aqueous phase (10) which can be recycled, at least in part, to the reaction stage in the form of a stream (3) devoid of heavy impurities harmful to the dehydration catalyst.

According to the process of the invention, the aqueous phase (10) is subjected to an oxidation stage (J) in the presence of oxygen, an oxygen-containing gas, hydrogen peroxide or ozone, preferably in the presence of oxygen or of an oxygen-containing gas, resulting in a stream (15) comprising essentially water, oxygen and $CO_2$ resulting from the subsequent degradation of the organic compounds and possibly nitrogen and argon. This stream (15) may then be advantageously recycled, completely or partly, to the glycerol dehydration stage a) without any risk of impurities accumulating on the dehydration catalyst. This makes it possible in particular to adjust the water content of the stream (5) containing glycerol that will feed the dehydration reactor (B). Preferably, a portion (18) of the stream (15) is removed from the process. The stream (18) comprises especially a portion of the water generated by the dehydration reaction and the organic matter oxidation reaction and the $CO_2$ generated by the oxidation of the organic matter. If this stream does not contain any pollutant, it can be discharged into the natural environment. Part of the energy contained in the stream leaving the oxidizer (J) in the form of a stream (15) may serve to preheat the feed (10) and/or (13) for this same oxidizer (J). In addition, part of the energy contained in the stream leaving the oxidizer (J) in the form of the stream (3) recycled to the dehydration stage a) may serve to preheat the glycerol solution in the mixing stage (A) before the reactive stream is sent to the dehydration reactor (B). If the dehydration stage a) is carried out in the gas phase, the energy contained in the stream leaving the oxidizer (J) in the form of the stream (3) may serve to vaporize the glycerol solution in the mixing stage (A) before the reactive stream is sent to the dehydration reactor (B). It should be noted that in this case, the transfer of energy of the stream (3) to the glycerol (1) takes place when the two streams are being mixed and therefore does not need any heat exchanger.

The oxidation stage (J), which consists in converting the impurities present in the stream (10) to the $CO_2$ and $H_2O$ state, may be carried out in various ways:

According to a first embodiment of the invention, a thermal oxidation is carried out in the gas phase in the presence of oxygen at a temperature above 700° C. in a thermal oxidation system (or oxidizer), usually consisting of a combustion chamber provided with a burner and with a primary heat exchanger for preheating the effluent to be treated, using the energy contained in the flue gases output by the combustion chamber. The stream is introduced into the combustion chamber where the temperature is maintained at a temperature above the auto-ignition temperature of the impurities to be oxidized, generally above 700° C., preferably above 750° C., optionally with an addition of fuel, such as natural gas, propane or light, medium or heavy fuel oil, so as to sustain the combustion if the concentration of organic compounds is insufficient. The oxygen needed for the reaction is provided by pure oxygen, oxygen-enriched air or air. Since the oxygen and the stream to be treated have to form a mixture that is as homogeneous as possible, it is preferable to add the oxygen upstream of the oxidation reactor. The residence time of the gases at the required temperature is typically around 0.6 to 2 seconds.

In a second embodiment of the invention, an oxidation is carried out in the gas phase in the presence of oxygen at a temperature ranging from 200° C. to 500° C. in the presence of a catalyst. As oxidation catalysts, it is typical to use solid catalysts consisting of an active species deposited on an inorganic, for example alumina or silica, support or on a metal-ceramic support. The active species are based on precious metals (platinum, palladium, rhodium or a combination of these metals) or else on metal oxides based on chromium, iron, molybdenum, tungsten, manganese, cobalt, copper or nickel, it being possible for these to be doped with precious metals. The catalysts may take the form of beads, pellets, granules, extrudates, bricks or monoliths. Hourly space velocities (gas flow rate/catalyst volume ratios) of the order of 10 000 to 50 000 $h^{-1}$ will typically be respected. According to this method of oxidation, it is also possible to add a fuel, such as natural gas or light, medium or heavy fuel oil, so as to sustain the combustion if the concentration of organic compounds is insufficient.

According to a third embodiment of the invention, a wet oxidation (subcritical oxidation) or a supercritical oxidation is carried out at a temperature above 150° C. and a pressure above 5 bar. The wet oxidation is carried out at temperatures between 150° C. and 330° C. and pressures of 5 to 150 bar. The residence time in the reactor is typically from 30 minutes to 3 hours. It will be advantageous to use a heterogeneous catalyst based on metal oxides or mixed oxides having a specific surface area ranging from 10 to 1000 $m^2/g$ containing a dispersed active compound such as Pt, Pd, Rh, Ru, Cu, Mn or Co. The hourly space velocity (the flow rate of the gas to be treated divided by the catalyst volume) is typically between 0.5 and 10 $h^{-1}$. Oxygen, oxygen-enriched air or air is injected into the reactor or upstream of the reactor. The supercritical oxidation is carried out at a temperature above 374° C. and at a pressure above 221 bar.

According to a fourth embodiment of the invention, the oxidation is carried out in the liquid phase in the presence of hydrogen peroxide or ozone, or a combination of these two reactants, which reactants may be activated, for example, by the use of UV radiation or by the use of catalysts such as iron(II) salts.

In all the embodiments of the invention, a stream (3) is obtained that may advantageously be completely or partially recycled to the glycerol dehydration stage a), without the risk of impurities accumulating on the dehydration catalyst. This stream (3) makes it possible in particular to adjust the water content of the glycerol-containing stream (5) that will feed the dehydration reactor (B).

In all cases, the energy contained in the stream leaving the oxidizer is advantageously used, at least partly, to preheat the stream entering the oxidizer. It may also be used to preheat the streams of material entering the first reaction stage, such as the glycerol, water and inert gases.

In the case of a gas-phase reaction and a gas-phase oxidizer, it is advantageous to use the high level of heat of the stream (3) to vaporize the glycerol stream (1), which ends up at a very high temperature. Moreover, the water needed for the reaction in the stream (5) is supplied directly in the gaseous state with a high thermal level, this being very advantageous in terms of energy.

According to a preferred embodiment, the gas-phase thermal or catalytic oxidizer (J) will be operated at a pressure 0.1 to 5 bar, preferably 0.2 to 2 bar, above that of the reactor (B). According to another preferred embodiment, the thermal or catalytic oxidizer will be operated at a pressure close to atmospheric pressure and the gas stream (3) is compressed before being injected into the reactor (B).

According to one embodiment of the process according to the invention (not represented in FIG. 1), the acrolein-enriched phase (9), which is freed from the heavy by-products and from a large part of the water, originating from stage b) for separation of the stream resulting from the dehydration stage a), is subjected to a purification treatment comprising absorption/distillation stages, such as those described, for example, for the acrolein stream produced by oxidation of propylene in the document Techniques de l'Ingénieur, Traité des Procédés [Techniques of the Engineer, Treatise on Processes], J 6 100 1-4.

The purification of the stream (9) comprising the acrolein, after cooling by one or more heat exchangers, generally comprises an absorption in water or a recycled aqueous stream to allow the non-condensable products to leave at the top and to recover, at the bottom, a dilute aqueous solution of acrolein.

This absorption can be carried out in a packed or plate column, preferably countercurrently. Advantageously, the non-condensable light compounds, such as nitrogen, oxygen, carbon monoxide and carbon dioxide, are removed at the top of the column.

The aqueous acrolein solution is subsequently separated by distillation. For this, use may be made of a sequence of distillation columns, as described, for example, in U.S. Pat. No. 3,433,840, or a single column, as described, for example, in documents EP 1 300 384 or EP 1 474 374. This distillation makes it possible to recover, on the one hand, a stream predominantly composed of water, most of which is generally recycled to the absorption stage, and, on the other hand, a gas or liquid stream comprising a content by weight of acrolein of greater than 80% and preferably >94% and a content by weight of water of less than 15%, with respect to the acrolein, and preferably <5%.

The stream (9) comprising acrolein can also be purified simply by distillation without prior absorption in water. This alternative is advantageously employed when the stream (9) comprises little in the way of non-condensable gases.

The liquid or gaseous acrolein stream, obtained on conclusion of the stages for purification of the stream (9), can then be used to prepare methylmercaptopropionaldehyde (MMP) by reaction with methyl mercaptan in the presence of a catalyst. The reaction of MMP, optionally purified, with hydrocyanic acid or sodium cyanide, carried out according to the Bücherer or Strecker synthesis well known to a person skilled in the art, then results either in methionine or in the hydroxy analogue of methionine, after conversion of the reaction product, as described in the document Techniques de l'Ingénieur, Traité Génie des procédés, J 6 410-1 to 9.

FIG. 3 shows a detailed diagram of a preferred embodiment of the acrolein manufacturing process according to the invention, the glycerol dehydration reaction being carried out in the gas phase.

The gas stream (5) feeding the dehydration reactor (B) is obtained in the mixing chamber (A) in which the glycerol is vaporized using the hot gases coming from the recycling (3) of the aqueous phase after the oxidation treatment carried out in the oxidizer (7), and also possibly from the recycling (2) of a gas stream predominantly containing $CO_2$ coming from the oxidizer (J). The glycerol stream (I) in liquid form, optionally preheated to a temperature of around 100° C. to 200° C. which may range up to 280° C., may be injected into this chamber with a cocurrent or countercurrent gas flow, via spray or atomization nozzles forming fine droplets in contact with the recycled stream (3) comprising essentially water, oxygen and $CO_2$, and possibly nitrogen, this stream being in gaseous form after the thermal oxidation treatment in the gas phase, or after an evaporation phase in the case of a thermal oxidation in liquid phase (not shown). The spray nozzles enable the liquid glycerol stream to be dispersed in the form of fine droplets by making mechanical adjustments (by varying the size and shape of the nozzle orifices, flow rate and pressure). The atomization nozzles also include the injection of a gas into the nozzles, as for example the stream (2), and generally make it possible to achieve droplet sizes smaller than those obtained with spray nozzles. These systems make it possible to form droplets smaller in size than 1 mm and preferably smaller than 300 μm. The finer the droplet size, the more rapid the stream (1) is evaporated.

In another embodiment, the intimate mixing of the liquid glycerol stream (1) and the recycled stream (3) is performed in a venturi-effect mixer before being injected into the reactor (B).

In the diagram shown in FIG. 3, the energy needed to preheat the stream (5) entering the reactor is provided by the superheated streams (3) and (2). Alternatively, a heat exchanger might be placed between the mixing unit (A) and the reactor (B).

A supply of oxygen, air or an oxygen-containing gas, which promotes the dehydration reaction, is supplied at (4).

The gaseous reaction stream (6) output by the reactor may be cooled in a heat exchanger (C) down to a temperature between 70° C. and 200° C. and preferably between 110° C. and 180° C. before it enters a condensation column (D), fitted with a condenser (E), enabling a liquid phase (8) comprising predominantly water and acrolein, which phase is recycled to the column (D), to be separated from the gas stream (9) comprising the acrolein produced. Generally, this stream (9) contains water in an acrolein/water weight ratio ranging from 1/0.02 to 1/3 and preferably from 1/0.5 to 1/2, but also the light by-products, such as acetaldehyde, propanaldehyde, acetone and optionally $O_2$ and inert gases CO and $CO_2$. In order to strip acrolein from the liquid stream (10) exiting at the bottom of the column (D), the latter may be fed at the bottom with a gas stream (7) comprising predominantly $CO_2$ coming from the oxidizer (J), the role of the said phase being to strip the acrolein. Other gas streams could be suitable, such as a nitrogen stream or steam stream, or another recycled stream of the installation. Alternatively, the acrolein may be stripped by reboiling at the bottom of the column (D) or by the addition of a stripping column fed at the top with the liquid stream (10) and at the bottom with a gas stream as described above.

The liquid stream (10) leaving the bottom of the absorption column, to which an aqueous stream (11) possibly containing glycerol and methanol coming from the purification of the glycerol starting material is optionally added, is vaporized in the heat exchangers (G) and (H) and then sent to the oxidizer (J) in gas form. Alternatively, only a portion of this aqueous stream is vaporized—that part comprising mostly water and light compounds—and is then sent in gaseous form to the oxidizer (J). The liquid vaporization residue, which is concentrated in heavier organics than water, is either injected in liquid form into the oxidizer (J) or is removed from the process.

The inlet temperature of the oxidizer (J) will be chosen to allow correct combustion of the organic matter, generally ranging from 200° C. to 500° C. in the case of a catalytic oxidation in the gas phase, and from 600° C. to 1200° C. in the case of a thermal oxidation. A supply of oxygen or air or oxygen-enriched air necessary for the thermal oxidation is carried out at (13). In the loop, it is possible to incorporate a gas stream (12) containing organic impurities, thus making it possible to incinerate gaseous effluents coming for example from the acrylic acid purification unit downstream of the acrolein manufacturing process. The heat exchanger (H) is used to recover the energy coming from the flue gases (15) output by the oxidizer in order to preheat the stream (14) at the inlet of the oxidizer. At the outlet of the oxidizer, the gas stream (16) is at least partly recycled to the dehydration stage (stream (3)), the remaining stream (17) being purged of some of the liquid water (18) via a heat exchanger (K) and recycled either in the form of a gas stream (7) at the bottom of the absorption column (D) or in the form of a gas stream (2) at the inlet of the mixing phase (A), as described above, it being possible to carry out a gas purge at (20).

Manufacture of Acrylic Acid

With reference to FIG. 2, for the implementation of the process according to the invention, the phase (9) enriched in acrolein and freed from the heavy by-products and from a large part of the water, originating from stage b) for separation of the stream resulting from the dehydration stage a), is subjected to a catalytic oxidation reaction d) in a reactor (M) in order to obtain a stream (22) comprising the desired acrylic acid. This stream is subsequently subjected, in a stage e), to one or more purification treatments (O), making it possible to recover purified acrylic acid (25). The reaction for the oxidation of the acrolein to give acrylic acid is carried out in the presence of molecular oxygen or of a mixture comprising molecular oxygen, at a temperature ranging from 200° C. to 350° C., preferably from 250° C. to 320° C., and under a pressure ranging from 1 to 5 bar, in the presence of an oxidation catalyst. Use is made, as an oxidation catalyst, of all types of catalyst well known to a person skilled in the art for this reaction. Use is generally made of solids comprising at least one element chosen from the list Mo, V, W, Re, Cr, Mn, Fe, Co, Ni, Cu, Zn, Sn, Te, Sb, Bi, Pt, Pd, Ru and Rh, present in the metallic form or in the oxide, sulphate or phosphate form. Use is made in particular of the formulations comprising Mo and/or V and/or W and/or Cu and/or Sb and/or Fe as main constituents.

The oxidation reactor (M) can operate as a fixed bed, as a fluidized bed or as a circulating fluidized bed. It is also possible to use a plate exchanger with a modular arrangement of the catalyst, such as described in the documents EP 995 491, EP 1 147 807 or US 2005/0020851.

The gas mixture (22) resulting from the oxidation reaction is composed, apart from the acrylic acid, of various compounds, such as:

light compounds which are non-condensable under the temperature and pressure conditions normally employed: $N_2$, unconverted $O_2$, CO and $CO_2$, formed in a small amount by the last oxidation or going around, by recycling, in the process, condensable light compounds: in particular the residual water from the preceding stage, generated by the dehydration reaction or present as diluent, unconverted acrolein, light aldehydes, such as formaldehyde and acetaldehyde, formic acid, acetic acid and propionic acid, residual heavy compounds from the preceding stage: furfuraldehyde, benzaldehyde, maleic acid, maleic anhydride, benzoic acid, phenol or protoanemonin.

In order to obtain acrylic acid corresponding to a certain technical grade, it is necessary to subject this mixture (22) to a purification sequence represented in part, for example, in FIG. 4:

The first stage of this purification phase consists of an extraction of acrylic acid by countercurrentwise absorption. For this, the gas mixture (22), optionally after cooling in a heat exchanger (N), is introduced at the bottom of an absorption column (P), where it encounters, countercurrentwise, a solvent (23) introduced at the column top, generally water. The light compounds which are non-condensable under the temperature and pressure conditions normally employed (respectively more than 50° C. and less than $2 \times 10^5$ Pa) are removed at the top of this absorption column in a stream (29). The solvent (23) employed in this column is water. The water might be replaced by a hydrophobic solvent with a high boiling point, as described, for example, in patents FR 2 146 386 and U.S. Pat. No. 5,426,221, and also in Patent FR 96/14397. The water used as absorbing solvent can be contributed by a source external to the process but can be composed, in all or part, of water resulting from recycling of an aqueous phase in the process, for example the water separated in the separating unit (D) or the water recovered from the top stream of an azeotropic drying column optionally present in the purification sequence. According to an alternative form, water is not added in the absorption column. The operating conditions of this absorption stage are as follows:

The gaseous reaction mixture is introduced at the column bottom at a temperature of between 130° C. and 250° C. The water is introduced at the column top at a temperature of between 10° C. and 60° C. The respective amounts of water and of gaseous reaction mixture are such that the water/acrylic acid ratio by weight is between 1/1 and 1/4. The operation is carried out at atmospheric pressure.

The absorption column (P) can be coupled to a column for the distillation of the very light compounds, essentially acrolein unconverted on conclusion of the reaction which is present at a low concentration in the aqueous acrylic acid solution recovered at the bottom of the absorption column. This distillation column (Q), which operates under a pressure of $6 \times 10^3$ to $7 \times 10^4$ Pa, is fed at the top by the stream (24) from the bottom of the preceding absorption column and makes it possible to remove, at the top, a stream (26) of acrolein-enriched acrylic acid which is at least partially recycled, via a condenser, in the form of a liquid stream (27), at the lower part of the absorption column, for final removal at the top of this same column, the remaining gas stream (28) being recompressed in a compressor (S) and optionally conveyed to the oxidizer present in the process for the manufacture of acrolein. There is thus obtained, after conclusion of these purification stages, an aqueous mixture (25) of acrylic acid in water (ratio by weight 1/1 to 4/1) freed from the bulk of the unconverted acrolein, which is referred to as "crude acrylic acid".

Depending on the grade desired for acrylic acid, this mixture will be subjected to additional treatments described in numerous patents, in particular to a dehydration stage which is carried out in the presence of a water-immiscible solvent for acrylic acid. This dehydration stage can be carried out by azeotropic distillation of the solvent, water and acrylic acid mixture, which makes it possible to take out the solvent/water azeotrope at the distillation top. The acrylic acid recovered at the bottom is subsequently subjected to a distillation of the light compounds (topping) and separation of the heavy compounds (tailing). A grade of acrylic acid referred to as "technical" is then obtained, which grade can subsequently be subjected to a subsequent purification, for example by fractional crystallization, to give a glacial grade.

Energy Optimization of the Process According to the Invention

Gas streams which have to be cooled and condensed and liquid streams which have to be vaporized are present in the process according to the invention. The use of compression systems, especially heat pumps, makes it possible to minimize the heat lost by making it possible to transfer heat from the coolest medium to the hottest medium. A heat pump is a thermodynamic device, the operation of which is based on the principle of the refrigerant compression cycle. When the refrigerant is compressed and passes from the gas state to the liquid state, an exothermic (condensation) phenomenon occurs which produces heat. Conversely, if the refrigerant is reduced in pressure, bringing it from the liquid state to the gas state, an endothermic (evaporation) phenomenon occurs which makes it possible to absorb heat and to cool down. Everything is based on the change of state used in a closed circuit.

In the process of the invention, use is advantageously made of a heat pump to recover the energy of condensation of the water of the reaction stream (6) at the outlet of the dehydration reactor and to vaporize the acrolein-depleted aqueous phase separated from the acrolein-enriched phase during stage b). The heat pump can operate with water or with any suitable refrigerant known to a person skilled in the art, such as, for example, 1,1,1,3,3-pentafluoropropane or 1,1,1,3,3-pentafluoropentane, or a composition comprising at least one hydrochloroolefin, such as 1-chloro-3,3,3-trifluoropropene or 2-chloro-3,3,3-trifluoropropene, or a composition comprising, by weight, from 1 to 50% of methyltetrahydrofuran and from 5 to 99% of nonafluorobutyl alkyl ether of formula $C_4F_9OR$, R comprising from 1 to 4 carbon atoms, such as described in Patent Application FR 2 928 648.

In the case where the dehydration reaction is carried out in the gas phase, the stream (6) exits from the reactor in the form of a gas mixture at a temperature ranging from 150° C. to 550° C. and preferably between 250° C. and 400° C. This stream is cooled by virtue of a first heat exchanger in order to bring it to a temperature ranging from 150° C. to 200° C. Generally, this heat exchanger makes it possible to recover energy by producing low pressure steam. A second heat exchanger makes it possible to cool this stream down to a temperature ranging from 70° C. to 120° C. and preferably from 90° C. to 110° C., so as to feed the absorption column (D), from where the liquid phase depleted in acrolein (10), separated from the gas phase enriched in acrolein (9), exits at the bottom. This liquid stream (10) is vaporized at a pressure 0.1 to 3 bar higher than the inlet pressure of the dehydration reactor by virtue of a third heat exchanger at a temperature ranging from 110° C. to 200° C. and preferably from 130° C. to 160° C., in order to obtain a gas phase that can be mixed with oxygen and then raised to a higher temperature in order to be injected into the thermal oxidizer.

The heat pump operating with a refrigerant which can be water or any other refrigerant is installed on the abovementioned second and third heat exchangers. A liquid stream is vaporized in the first heat exchanger and then compressed in a compressor at a pressure of between 2 and 30 bar and preferably from 2 to 8 bar at a temperature of 110° C. to 200° C. The stream obtained is condensed in the second heat exchanger and then reduced in pressure and cooled in order to restore the liquid stream, thus forming a loop between the two heat exchangers.

The use of such a heat pump will be described in more detail in Example 3, with reference to FIG. 5 in which the heat pump is shown dotted.

In another configuration shown in FIG. 3, in which the reaction is carried out in the gas phase, the stream (6) leaving the dehydration reactor is cooled by a first heat exchanger (C) down to a temperature ranging from 130° C. to 200° C. and preferably 150° C. to 180° C., and is then injected directly into the condensation column (D). The thermal equilibrium of the column (D), enabling the liquid acrolein-depleted phase (10) to leave from the bottom and the acrolein-enriched gas phase (9) to leave from the top, is provided by the cooling heat exchanger (E) that operates at a temperature ranging from 50° C. to 100° C. and preferably 60° C. to 90° C. The liquid stream (10) is vaporized at a pressure 0.1 to 3 bar higher than the inlet pressure of the dehydration reactor by virtue of the heat exchanger (G) at a temperature ranging from 120° C. to 200° C. and preferably from 130° C. to 160° C., in order to obtain a gas phase that can be mixed with oxygen, and then raised to a higher temperature before being injected into the thermal oxidizer. The heat pump may be installed on the heat exchangers (E) and (G), the heat exchanger (E) being used to vaporize the refrigerant, said refrigerant then being compressed, then condensed in the heat exchanger (G) before being expanded and then sent to the heat exchanger (E).

Compression systems may also be used in a configuration exemplified in FIG. 3 in which the dehydration reaction and the oxidation stage are carried out in the gas phase and in which the gas stream (6) leaving the dehydration reactor is cooled by one or more heat exchangers (C), then recompressed by a compressor (not shown in FIG. 3) before being injected into the condensation column (D). The column (D) and the heat exchanger(s) (E) operate at a pressure at least 1 bar and preferably at least 2 bar above that of the reactor (B). The liquid stream (10) recovered from the bottom is then vaporized via the heat exchanger(s) (G) that operate at a pressure at least 0.5 bar and preferably at least 1.5 bar below that of the heat exchangers (C) and (E) and at a pressure above the oxidation reactor (J) which itself operates at a pressure above that of the reactor (B).

Under these conditions, the condensation taking place at the top of the column (D) may be coupled to the vaporization at the outlet of the pump (F), that is to say the gas stream leaving the top of the column can be cooled directly by the liquid stream leaving the pump (F), which will itself be reheated. In other words, the acrolein-depleted aqueous phase coming from stage b) is vaporized at least partly by a heat exchanger (or exchangers), providing cooling on leaving stage a) and in stage b), i.e. the heat exchangers (C), (E) and (G) may be coupled.

Advantageously, the gas stream (6) exiting from the dehydration reactor can be cooled by the heat exchanger (C) down to a low temperature, typically of 110° C. to 160° C., so as to produce steam in the heat exchanger (C), which steam can be used at other places in the process for the production of acrolein or acrylic acid or outside the process.

The heat pump(s) employed in the process according to the invention can also be used to produce steam at a sufficient thermal level for it(them) to have a use in or outside the process.

The process according to the invention thus contributes to reducing fuel consumption and the $CO_2$ discharge into the atmosphere.

The bioresourced acrylic acid obtained according to the process of the invention can be used for the manufacture of homopolymers and copolymers produced by polymerization of acrylic acid and optionally of other unsaturated monomers, for example the manufacture of superabsorbent polymers obtained by polymerization of said partially neutralized acid or by polymerization of said acid, followed by partial neutralization of the polyacrylic acid obtained.

The bioresourced acrylic acid obtained according to the process of the invention can also be used for the manufacture of polymers or copolymers by polymerization of the derivatives of said acid in the ester or amide form.

EXPERIMENTAL PART

A simulation using ASPEN software was used to illustrate the process according to the invention. The percentages are expressed as % by weight. The entities having a content of less than 1% will not be mentioned. The pressures are expressed in bar absolute.

Example 1 (with Reference to FIG. 3)

Gas-Phase Dehydration of Glycerol to Produce Acrolein and Thermal Oxidation in the Gas Phase on the Recycled Aqueous Phase A glycerol liquid stream (1) preheated to 200° C. (17.5 t/h; 98.4% glycerol, 1.1% water) and a gas stream (2) (2.1 t/h, 191° C., 7 bar; 85.3% $CO_2$, 9.4% water, 4.5% $O_2$) are injected via a spray nozzle (A) into a recycled gas stream (3) (70.8 t/h, 491° C., 2.8 bar; 49.5% water, 47.6% $CO_2$, 2.5% $O_2$) mixed with an oxygen stream (4) (2.6 t/h). Spraying the glycerol as fine droplets enables it to be vaporized over a short distance. The resulting gas stream (5) (93.1 t/h, 320° C., 2.7 bar; 18.5% glycerol, 38.1% water, 4.8% oxygen, 38.1% $CO_2$) is sent to a fixed-bed multi-tube reactor (B) containing 35 m³ of a heterogeneous acid dehydration catalyst and coupled to a molten salt bath. Leaving this reactor is a gas stream (6) at 320° C. and at 1.7 bar (45.3% water, 3.8% oxygen, 9.0% acrolein, 38.6% $CO_2$). This stream is cooled down to 160° C. in a heat exchanger (C) and sent to an absorption column (D) at the bottom of which is injected a gas stream (7) (9.0 t/h, 83° C.; 85.3% $CO_2$, 9.4% water, 4.5% $O_2$), the said column having a condenser (E) at the top. Leaving this condenser (E) are a liquid phase (8) (40.1 t/h, 70° C.), which is sent to the column (D), and an acrolein-enriched gas stream (9) (64.3 t/h), which leaves at 70° C. under a pressure of 1.6 bar and comprises 67.9% $CO_2$, 13.1% acrolein, 9.3% water, 6.2% $O_2$ and 1.1% acetaldehyde.

The acrolein-depleted liquid stream (10) leaving the bottom of the column (D) (37.8 t/h, 77° C.; 97.9% water, 0.005% acrolein, 0.5% glycerol, 0.4% acetic acid, 0.3% acrylic acid, 0.4% acetol, 0.5% other heavy organic compounds) is mixed with an aqueous stream (11) (1.1 t/h; 96.8% water, 1.9% methanol, 1.3% glycerol) and then pumped with a pump (F), then mixed with a gas stream (12) (57.7 t/h, 190° C., 2.9 bar; 76.2% $CO_2$, 18.8% water, 1.7% $O_2$, 1.3% CO) and with oxygen (13) (4.3 t/h) and heated to 186° C. via the heat exchangers (G). The resulting stream (14) (100.9 t/h, 2.8 bar; 48.4% water, 43.6% $CO_2$, 5.3% $O_2$, 1.5% organics, 0.7% CO) is preheated to 458° C. via the heat exchanger (H) and injected into an adiabatic catalytic oxidation reactor (J) that contains 6 m³ of a platinum-on-alumina oxidation catalyst. The flue gases (15) leaving the reactor (J) (100.9 t/h, 700° C., 2.8 bar; 49.5% water, 47.6% $CO_2$, 2.5% $O_2$) are cooled down to 491° C. via the heat exchanger (H). The resulting stream (16) is divided into a stream (3), already described, and a stream (17) (30.1 t/h, 491° C., 2.8 bar). The stream (17) is cooled down to 83° C. by means of the heat exchangers (K). The liquid phase (18) comprising 99.9% water is removed. The gas phase (19) (83° C., 2.7 bar; 85.3% $CO_2$, 9.4% water, 4.5% $O_2$) is divided into a stream (7), already described, a stream (20) which is removed and a stream (21) which is compressed to form the stream (2), already described.

Example 2 (with Reference to FIG. 4)

Production of Acrylic Acid

The gas stream (9) of Example 1 (64.3 t/h, 70° C., 1.6 bar; 67.9% $CO_2$, 13.1% acrolein, 9.3% water, 6.2% $O_2$, 1.1% acetaldehyde) is heated to 160° C. by a heat exchanger (L) and then injected into a second fixed-bed multi-tube reactor (M) comprising an oxidation catalyst and coupled to a molten salt bath, enabling the heat produced by the reaction to be removed. The gas stream (22) (64.3 t/h; 68.4% $CO_2$, 15.8% acrylic acid, 9.5% water, 1.6% oxygen, 1.1% carbon monoxide, 1.0% acetic acid) leaving this reactor is cooled down to 160° C. by the heat exchanger (N) and then injected into the bottom of the absorption column (P). Injected into the top of this column is a 9 t/h stream (23) of water at 25° C. Recovered from the bottom of this column is a liquid phase (24) (16.6 t/h, 80° C.; 62.0% acrylic acid, 30.9% water, 4.0% acetic acid, 2.4% formic acid). This liquid phase is sent to a column (Q) operating under vacuum, enabling an acrylic acid stream (25) (15.6 t/h; 65% acrylic acid, 27.8% water, 4.2% acetic acid, 2.6% formic acid) to be recovered. The gas stream (26) (0.9 t/h, 69° C., 0.3 bar) is sent from the top of the column (Q) to a condenser, making it possible to obtain a liquid phase (27), which is returned to the column (P), and a gas phase (28) which feeds a vacuum set (R). The vent from this vacuum set is combined with the gas phase (29) from the column (P) (57.7 t/h, 74° C.; 76.2% $CO_2$, 18.8% water, 1.7% $O_2$, 1.3% CO). This stream is recompressed by the compressor (S) and forms the stream (12) described in Example 1.

Example 3 (with Reference to FIG. 5)

Gas-Phase Glycerol Dehydration in Order to Produce Acrolein, which is Oxidized to Acrylic Acid and Thermal Oxidation in the Gas Phase on the Recycled Aqueous Phase and with a Heat Pump A glycerol liquid stream (1) preheated to 210° C. (17.4 t/h; 99.0% glycerol) is injected via a spray nozzle (A) into a recycled gas stream (3) (62.5 t/h, 485° C., 2.8 bar; 68.1% water, 28.7% $CO_2$, 2.9% $O_2$) and mixed with an oxygen stream (4) (2.6 t/h). Spraying the glycerol as fine droplets enables it to be vaporized over a short distance. The resulting gas stream (5) (82.5 t/h, 320° C., 2.8 bar, 20.8% glycerol, 51.7% water, 5.3% oxygen, 21.8% $CO_2$) is sent to a fixed-bed multi-tube reactor (B) containing a heterogeneous dehydration catalyst and coupled to a molten salt bath. Leaving this reactor is a gas stream (6) (59.8% water, 4.2% oxygen, 10.8% acrolein, 22.4% $CO_2$) at 320° C. and at 1.8 bar. This stream is cooled down to 160° C. in a heat exchanger (C1) from which a small stream of liquid heavy products (6a) (68 kg/h) and a gas phase are recovered, which gas phase is cooled down to 102° C. via a heat exchanger (C2). This results in a liquid phase (6b) (26.7 t/h; 97% water) and a gas phase (6c) (42.1% water, 33.1% $CO_2$, 6.3% $O_2$, 14.7% acrolein, 1.3% acetaldehyde, 1.1% CO) which is sent to an absorption column (D). A gas stream (7) (35.9 t/h, 123° C.; 76.3% $CO_2$, 16.5% water, 3.0% CO, 1.9% $O_2$) is also injected into this column (D). Above the column (D), a condenser (E) generates a liquid phase (8) (22.6 t/h, 74° C., 1.7 bar), which is returned to the column (D), and an acrolein-enriched gas stream (9) (69.5 t/h, 74° C., 1.7 bar) comprising 65.9% $CO_2$, 12.1% acrolein, 10.8% water, 6.0% $O_2$, 2.4% CO, 1.3% acetaldehyde.

The gas stream (9) is heated to 240° C. by a heat exchanger (L) and then injected into a second fixed-bed multi-tube reactor (M), comprising an oxidation catalyst and coupled to a molten salt bath, enabling the heat produced by the reaction to be removed. The gas stream (22) (69.5 t/h; 66.4% $CO_2$, 14.6% acrylic acid, 11.0% water, 2.6% carbon monoxide, 1.7% oxygen, 1.1% acetic acid) leaving this reactor is cooled down to 160° C. by the heat exchanger (N) and then injected into the absorption column (P). A 6.5 t/h stream (23) of water at 25° C. is injected into the top of this column. Recovered from the bottom of the column is a liquid phase (24) which is sent to a column (Q) operating under vacuum, enabling an acrylic acid stream (25) (15.5 t/h; 64.9% acrylic acid, 26.7% water, 4.9% acetic acid, 3.0% formic acid) to be recovered. The gas stream (26) (1.6 t/h, 72° C., 0.3 bar) is sent from the top of the column (Q) into a condenser and then into the column (P). The gas phase (29) (60.5 t/h, 72° C., 1.1 bar; 76.3% $CO_2$, 16.5% water, 1.9% $O_2$, 3.0% CO) from the column (P) is partly recompressed up to 1.7 bar by the compressor (S) and forms the stream (7) described above. The other part is compressed to 2.9 bar via the compressor (T) in order to give the stream (30).

The acrolein-depleted liquid stream (10) (22.2 t/h, 85° C.; 98.9% water, 0.03% acrolein) leaving the bottom of the column (D) is mixed with the stream (6b), pumped by a pump (F) and then vaporized in the heat exchangers (G1) and (G2) in order to give a gas stream (14a) (48.3 t/h, 135° C., 2.9 bar; 98.2% water) and a liquid stream (14b) which is mixed with the stream (6a) and injected directly into the thermal oxidizer (J). The streams (14a) and (30) are mixed with an oxygen stream (32) (4.6 t/h) in order to form a stream (14c) which is heated via the heat exchangers (H) and (K) to 977° C. and then injected into the thermal oxidizer. The resulting stream (15) (79.3 t/h, 1199° C.; 68.1% water, 28.7% $CO_2$, 2.9% $O_2$) leaving the thermal oxidizer is divided into a stream (18a) (16.8 t/h) which is cooled via the heat exchanger (H) down to 189° C. and then removed, and a stream (17), which is cooled via the heat exchanger (K) down to 485° C. to form the stream (3) already described.

A heat pump operating with steam is installed on the heat exchangers (C2) and (G1) and is shown by the dotted lines. A liquid water stream (33) (26.2 t/h, 25° C.) is vaporized in the heat exchanger (C2) (100° C., 1 bar) and then compressed by the compressor (R) to 3.5 bar at 270° C. The resulting stream (35) is condensed in the heat exchanger (G1), before being expanded and cooled to give the stream (33).

Example 4 (According to the Invention)

A dehydration acid catalyst is prepared by impregnating the pore volume with an aqueous phosphotungstic acid solution (3.9 g of phosphotungstic acid in 5.7 g of water) on a titanium oxide (15.4 g) reduced to a particle size of 300-500 µm. The catalyst is dried in a vented oven at 110° C. and then calcined for 3 hours at 500° C. A volume of 7 ml of the dehydration catalyst is introduced into a 316 l stainless steel reactor of 13 mm diameter placed vertically in an oven heated to 280° C.

A 15 g/h flow rate of a solution comprising 50 wt % pure glycerol and 50% water is mixed with a flow of oxygen and with a flow of nitrogen of 1.2 and 18 Nl/h respectively and then sent to a vaporizer which heats the mixture to 280° C. and is connected to the reactor.

The gaseous effluents leaving the reactor are either sent to two traps in series initially containing 120 and 80 grams of water chilled to 0° C., so as to completely trap the acrolein in order to carry out a material balance, or sent to a tank cooled to 0° C. so as to trap most of the water and the heavy products produced by the reaction. The pressure drop across the reactor is measured throughout the experiment.

A material balance is carried out with the water-filled traps in series from time t=2 hours to t=3 hours 30 minutes on the one hand and from time t=21 hours to t=22 hours 30 minutes, the glycerol and acrolein content in the traps being measured by gas chromatography. The glycerol conversion and acrolein yield are calculated according to the following formulae:

glycerol conversion (%)=((moles of glycerol injected into the reactor during the balance)−(moles of glycerol recovered in the two traps))/(moles of glycerol injected into the reactor during the balance)×100;

acrolein yield (%)=(moles of acrolein recovered in the two traps)/(moles of glycerol injected into the reactor during the balance)×100.

The results of the experiment are given in Table 1 below.

Moreover, most of the water and the heavy products were collected in the tank between time t=1 hour and time t=2 hours, and also between time t=3 hours 30 minutes and time t=21 hours. This aqueous solution was then treated for 2 hours in the rotary evaporator heated to 30° C. and in a partial vacuum, so as to evaporate the acrolein. The collection in the tank and the evaporation serve to simulate step (D) shown in FIG. 1.

To simulate steps (J), (A) and (B) of FIG. 1, a second reactor, containing 1.5 ml of a Haldor Topsoe CK307 oxidation catalyst, was coupled to the reactor containing the dehydration catalyst. A 5.5 g/h stream of the aqueous solution recovered is mixed with an oxygen stream and with a nitrogen stream of 2.4 and 18 Nl/h respectively and then sent to a vaporizer which heats the mixture to 300° C. and is connected to the reactor containing the oxidation catalyst. A 9.4 g/h stream of an 80% aqueous glycerol solution is injected between the oxidation reactor and the dehydration reactor. The oxidation reactor is maintained in a 300° C. zone and the dehydration reactor in a 280° C. zone.

The material balances are carried out as above and the results are given in Table 1.

Example 5 (Comparative)

In the same way, as in Example 4, the glycerol dehydration reaction was carried out with a solution comprising 50 wt % pure glycerol and 50% water, and most of the water and the heavy products, which were subjected for 2 hours in the rotary evaporator heated to 30° C. and in a partial vacuum, so as to evaporate the acrolein, was collected in a tank.

The recovered aqueous solution containing a mixture of water and heavy recycled products was then mixed directly with pure glycerol in order to prepare a 50% glycerol solution, and the glycerol dehydration experiment was repeated. For 3 hours 30 minutes, a pressure drop of 0.1 bar across the reactor was observed, the pressure then being progressively increased in order to reach 0.3 bar after 5 hours and exceed 1 bar after 7 hours. The experiment could not be continued further because of the exponential increase in the pressure drop.

The results are given in Table 1.

When recycled water containing heavy products is used, a very rapid rise in pressure after blocking the reactor was observed.

TABLE 1

|  | Glycerol conversion after 2 h/21 h (%) | Acrolein yield after 2 h/21 h (%) | Pressure drop after 2 h/5 h/21 h (bar) |
|---|---|---|---|
| Example 4: glycerol/water | >99%/80% | 70%/48% | 0.1/0.1/0.1 |
| Example 4: glycerol/recycled water condensate with oxidation reactor | >99%/79% | 70%/46% | 0.1/0.1/0.1 |
| Example 5 (comparative example): glycerol/water and heavy products recycled with no oxidation step | >99%/— | 70%/— | 0.1/0.3/>1 |

Example 6

Dehydration of Glycerol in the Gas Phase in Order to Produce Acrolein, which is Oxidized to Acrylic Acid, and Thermal Oxidation in the Gas Phase at Atmospheric Pressure on the Recycled Aqueous Phase A liquid glycerol stream (1) (17.4 t/h; 99.0% glycerol) preheated to 275° C. is injected via a venturi mixer into a recycled gas stream (3) (50.6 t/h, 442° C., 3.0 bar; 59.1% nitrogen, 25.3% water, 12.1% $CO_2$, 2.5% $O_2$, 1.0% argon), mixed with a stream of air (4) (20.6 t/h, 172° C., 3.0 bar) and with steam (4.3 t/h, 134° C., 3.0 bar). The venturi-effect mixer serves to vaporize the glycerol over a short distance.

The resulting gas stream (5) (92.8 t/h, 240° C., 2.8 bar; 18.5% glycerol, 18.5% water, 6.4% oxygen, 6.6% $CO_2$, 49.0% nitrogen) is sent to a fixed-bed multi-tube reactor (B) containing a heterogeneous dehydration catalyst and coupled to a molten salt bath. Leaving this reactor is a gas stream (6) (49.0% nitrogen, 25.7% water, 5.4% oxygen, 9.0% acrolein, 7.2% $CO_2$) at 320° C. and at 1.8 bar. This stream is cooled to 193° C. in a heat exchanger (C1) and then to 120° C. in a heat exchanger (C2), from which a small stream of liquid heavy products (6b) (0.2 t/h) and a gas phase (6c) (92.6 t/h, 120° C., 1.7 bar; 49.1% nitrogen, 25.8% water, 7.2% $CO_2$, 5.4% $O_2$, 9.1% acrolein) are recovered, which gas phase is sent to an absorption column (D). At the top of the column (D), a condenser (E) generates a liquid phase (8) (14.3 t/h, 74° C., 1.7 bar) which is returned to the column (D) and an acrolein-enriched gas stream (9) (79.4 t/h, 74° C., 1.7 bar) which contains 8.4% $CO_2$, 10.5% acrolein, 14.2% water, 6.3% $O_2$ and 57.3% nitrogen. The gas stream (9) is heated to 240° C. by the heat exchanger (C1) already described, and then injected into a second fixed-bed multi-tube reactor (M) comprising an oxidation catalyst and coupled to a molten salt bath, enabling the heat produced by the reaction to be removed. The gas stream (22) (79.4 t/h; 8.8% $CO_2$, 12.7% acrylic acid, 14.4% water, 57.3% nitrogen, 2.6% oxygen) leaving this reactor is cooled down to 160° C. by the heat exchanger (N) and then injected into the absorption column (P). A 10.4 t/h stream (23) of water at 25° C. is injected into the top of this column. Recovered from the bottom of the column is a liquid phase (24) which is sent to a column (Q) operating under vacuum, enabling an acrylic acid stream (25) (18.2 t/h; 55.1% acrylic acid, 38.6% water, 3.7% acetic acid, 2.2% formic acid) to be removed from the bottom of the column (Q). The gas stream (26) is sent from the top of the column (Q) into a condenser and then into the column (P). The gas phase (29) (71.6 t/h, 70° C., 1.1 bar) from the column (P) is composed of 9.8% $CO_2$, 20.6% water, 2.9% $O_2$, 1.0% argon, 1.0% CO and 63.5% nitrogen.

The acrolein-depleted liquid stream (10) (13.2 t/h, 89° C.; 95.4% water, 1.0% hydroxy-propanone) leaving the bottom of the column (D) is mixed with the stream (6b) and with a stream resulting from the purification of the acrylic acid stream (25) (1.2 t/h; 100% organic compounds) and with another stream (1.2 t/h) of recycled water. The mixture is vaporized via the heat exchanger (G) in order to give a gas stream (14a) (15.4 t/h, 133° C., 1.9 bar; 88.4% water, 1.3% acrylic acid, 5.1% acetic acid, 2.7% formic acid) and a liquid stream (14b) (0.4 t/h) which is directly injected into the thermal oxidizer (J). The streams (14a) and (29) are mixed with a stream (32) of air (40.5 t/h, 1.2 bar) and of natural gas (1.0 t/h) in order to form a stream (14c) which is heated via the heat exchanger (H) to 450° C. and then injected into the thermal oxidizer, which operates at atmospheric pressure. The resulting stream (15) (128.9 t/h, atmospheric pressure, 1026° C.; 25.3% water, 12.1% $CO_2$, 2.5% $O_2$, 59.1% nitrogen, 1.0% argon) leaving the thermal oxidizer is cooled down to 702° C. by the heat exchanger (H) already described and by the heat exchanger (H1) down to 670° C. before being divided into a stream (18a) (78.4 t/h), which is cooled down to 170° C. via the heat exchangers (H2) and (H3) and then removed via a duct, and a stream (17) (50.6 t/h). The stream (17) is cooled via the heat exchanger (K) down to 160° C. and then compressed to 3.0 bar and 352° C. and superheated to 442° C. via the heat exchanger (H1) already described in order to form the stream (3) already described.

The invention claimed is:

1. Process for the manufacture of acrolein from glycerol comprising at least the stages of:
   a) subjecting glycerol to a dehydration reaction to obtain an aqueous stream comprising acrolein;
   b) separating the stream resulting from stage a) into an acrolein-rich phase and an acrolein-depleted aqueous phase; and
   c) recycling all or part of the acrolein-depleted aqueous phase to stage a), characterized in that said acrolein-depleted aqueous phase is subjected to oxidation, in the presence of oxygen, oxygen-containing gas, hydrogen peroxide or ozone, before being recycled to stage a).

2. Process according to claim 1, comprising the step of purifying said acrolein-rich phase by absorption and/or distillation.

3. Process for the manufacture of acrylic acid from glycerol comprising at least the stages of:

a) subjecting glycerol to a dehydration reaction to obtain an aqueous stream comprising acrolein;
b) separating the stream resulting from stage a) into an acrolein-rich phase and an acrolein-depleted aqueous phase;
c) recycling all or part of the acrolein-depleted aqueous phase to stage a);
d) subjecting the acrolein-rich phase to a catalytic oxidation reaction to obtain a stream comprising acrylic acid;
e) subjecting the stream resulting from stage d) to one or more purification treatments and recovering purified acrylic acid, characterized in that said acrolein-depleted aqueous phase is subjected to an oxidation stage, in the presence of oxygen, oxygen-containing gas, hydrogen peroxide or ozone, before being recycled to stage a).

4. Process according to claim 1, characterized in that the oxidation is a thermal oxidation in the gas phase in the presence of oxygen at a temperature above 700° C.

5. Process according to claim 1, characterized in that the oxidation is a catalytic oxidation in the gas phase in the presence of oxygen, an oxidation catalyst, and at a temperature ranging from 200° C. to 500° C.

6. Process according to claim 1, characterized in that the oxidation is a wet oxidation or supercritical oxidation at a temperature above 150° C. and a pressure above 5 bar, in the presence of oxygen or air.

7. Process according to claim 1, characterized in that the oxidation is an oxidation in the liquid phase in the presence of hydrogen peroxide or ozone, or a combination thereof, optionally activated by UV radiation or iron(II) salt catalysts.

8. Process according to claim 1, characterized in that the energy contained in the stream leaving the stage for oxidizing the acrolein-depleted aqueous phase is used to preheat the stream entering this stage.

9. Process according to claim 3, characterized in that the aqueous phase recycled to the dehydration stage a) is in the form of the gas stream that vaporizes a glycerol stream before said dehydration reaction.

10. Process according to claim 9, characterized in that the glycerol stream is injected into a mixing chamber with spray or atomization nozzles optionally including a gas stream comprising $CO_2$ coming from the stage for oxidizing the acrolein-depleted aqueous phase.

11. Process according to claim 1, characterized in that stage a) is carried out in the gas phase and a heat pump is used to condense the gaseous reaction stream coming from stage a) and to vaporize the acrolein-depleted aqueous phase separated from the acrolein-enriched phase during stage b).

12. Process according to claim 1, characterized in that stage a) and the stage for oxidizing the acrolein-depleted aqueous phase are carried out in the gas phase, and a heat pump is used to condense the acrolein-depleted phase during stage b) and to vaporize said acrolein-depleted aqueous phase on leaving stage b).

13. Process according to claim 1, characterized in that stage a) and the stage for oxidizing the acrolein-depleted aqueous phase are carried out in the gas phase, and the acrolein-depleted aqueous phase coming from stage b) is vaporized at least partly by a heat exchanger (or exchangers), providing cooling on leaving stage a) and in stage b).

14. Process according to claim 13, characterized in that the cooling of the streams on leaving stage a) and in stage b) is operated at a pressure at. least 0.5 bar above that for the vaporization of the acrolein-depleted aqueous phase coming from stage b).

\* \* \* \* \*